United States Patent [19]

Hansen

[11] Patent Number: 5,521,957
[45] Date of Patent: May 28, 1996

[54] X-RAY IMAGING SYSTEM

[76] Inventor: Steven J. Hansen, 6610 N. Desert Fairways, Paradise Valley, Ariz. 85253

[21] Appl. No.: 213,670

[22] Filed: Mar. 15, 1994

[51] Int. Cl.$^6$ .................................................. H05G 1/02
[52] U.S. Cl. ........................... 378/198; 378/196; 378/197
[58] Field of Search ................................. 378/198, 195, 378/196, 197

[56] References Cited

U.S. PATENT DOCUMENTS 2,846,587  8/1958  Thurow ...................................... 378/196
4,879,737  11/1989  Grady ........................................ 378/196
5,008,921  4/1991  Kaul et al. ................................. 378/198

*Primary Examiner*—Craig E. Church
*Attorney, Agent, or Firm*—Tod R. Nissle

[57] ABSTRACT

A portable X-ray imaging machine includes a X-ray source and a X-ray image receptor. The source and the receptor are movable simultaneously along a line parallel to a patient reclined on the top of an examination table. The X-ray machine is readily transportable between and fixedly secured in a plurality of rooms in a hospital or other medical facility.

5 Claims, 1 Drawing Sheet

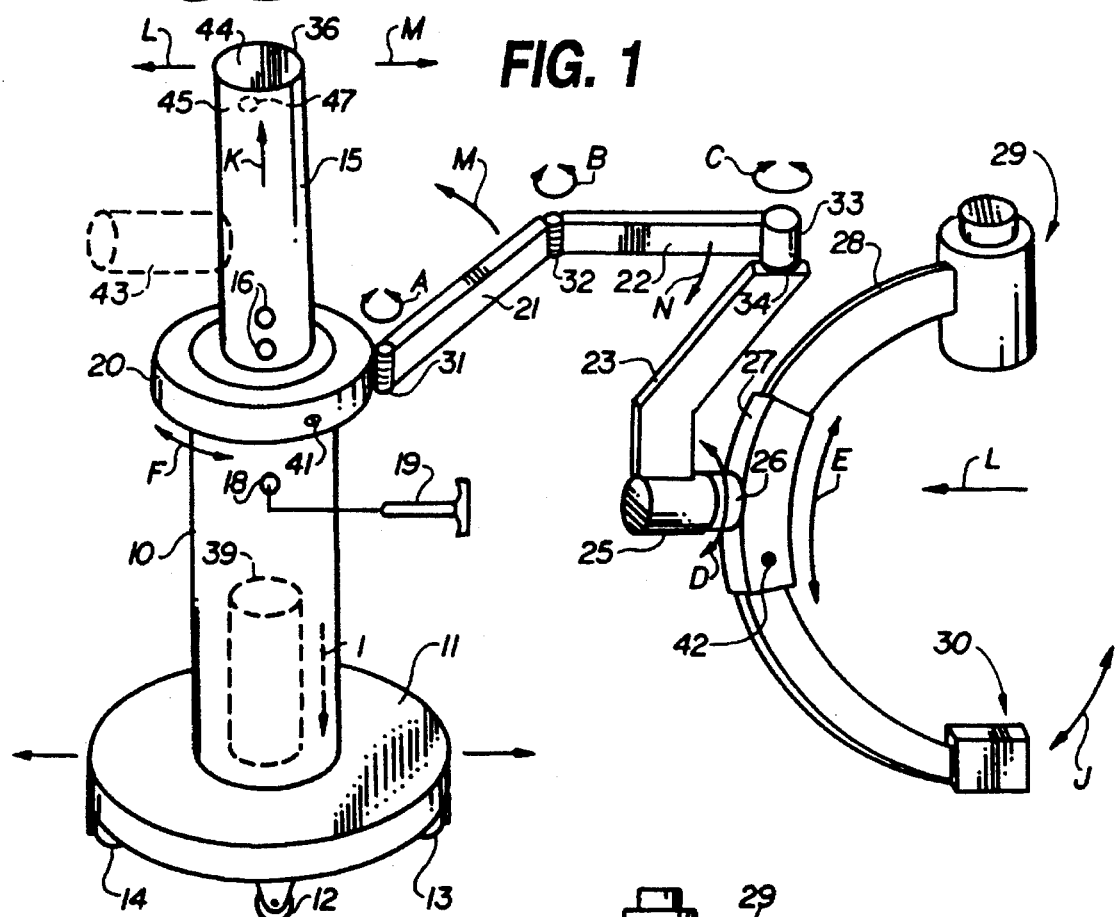
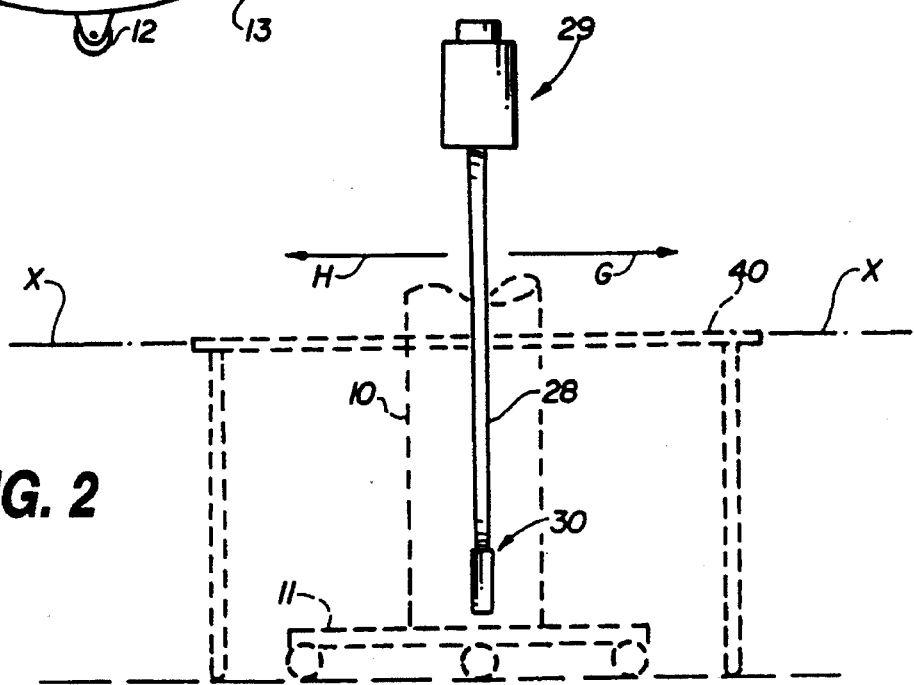

X-RAY IMAGING SYSTEM

This invention relates to X-ray imaging systems.

More particularly, the invention relates to an X-ray imaging system which is readily transported between and fixedly secured in a plurality of rooms in a hospital or other medical facility.

In a further respect, the invention relates to a portable X-ray imaging machine which includes and permits the x-ray source and the X-ray image receptor carried on the machine to move simultaneously along a line parallel to a patient reclined on the top of an examination table.

X-ray imaging equipment is well known in the art. Such equipment ordinarily is massive, is heavy, is permanently secured in the wall, ceiling or floor of a room in a building structure, and, is prohibitively expensive. Permanently securing such X-ray imaging equipment is desirable because the size of the equipment makes it difficult to handle. Further, the equipment typically includes a large C-shaped arm which carries an X-ray source and an X-ray image receptor. In use, a patient is reclined on the top of an examination table intermediate the X-ray source and the X-ray image receptor. The receptor receives the image produced after X-rays from the source pass through a patient. The large C-shaped arm extends out away from the equipment and above the floor. Consequently, if the equipment were not permanently anchored in the building structure, a large counterweight would have to be used to prevent the torque produced by the C-arm from causing the equipment to tip over. Such a counterweight would, at best, make the equipment unwieldy and difficult to maneuver.

Finally, transporting patients to the room housing prior art X-ray imaging equipment is, while a necessity, often undesirable when a patient is gravely ill or when it is awkward and time consuming to move the patient.

Accordingly, it would be highly desirable to provide improved X-ray imaging apparatus which would not have to be permanently anchored in a building structure, and which could be easily and safely maneuvered by a person of minimal physical strength.

Therefore, it is a principal object of the invention to provide improved X-ray imaging equipment.

A further object of the invention is to provide portable X-ray imaging equipment of the type including a large C-shaped arm which carries an X-ray source and a X-ray image receptor in spaced relationship such that a table top and patient reclining on the table top can be positioned intermediate the X-ray source and the X-ray image receptor.

Another object of the invention is to provide portable X-ray imaging equipment of the type described in which the large C-shaped arm can be safely extended from the equipment to take an X-ray image of a patient and in which the equipment can be safely moved without fear that equipment will tip due to the weight of the C-shaped arm.

Still a further object of the invention is to provide X-ray imaging equipment of the type described in which the C-shaped arm can be readily moved along a line generally parallel to a patient reclining on the top of an examining table.

These and other, further and more specific objects and advantages of the invention will be apparent to those skilled in the art from the following detailed description thereof, taken in conjunction with the drawings, in which:

FIG. 1 is a perspective view illustrating portable X-ray imaging apparatus constructed in accordance with the principles of the invention;

FIG. 2 is a front elevation view illustrating the mode of operation of the C-shaped X-ray imaging arm of the apparatus of FIG. 1; and, FIG. 3 is a top view of FIG. 2 showing only the longitudinal axis of the examining table and two possible paths of travel of the X-ray source and the X-ray image receptor on the C-shaped arm of FIG. 2.

Briefly, in accordance with my invention, I provide an improved X-ray system. The system includes a plurality of examining rooms in a building structure, each of the rooms including a ceiling. The system also includes a portable X-ray machine which includes a base, a plurality of ground-engaging wheels attached to the base; a neck having a distal end and mounted in the base for adjustment between at least two operative positions, a first operative storage position, and a second operative extended position with the distal end moved a selected distance away from the base; a source of X-rays; an image receptor for receiving X-rays; an arm having a first end attached to the X-ray source and a second end attached to the receptor, the arm being shaped such that the source and receptor are spaced apart; and, an articulated linkage assembly interconnecting the base and the arm. The linkage assembly is operable to move simultaneously the arm linearly toward or away from the base, and through an arc generally parallel to the ground such that the arm can be moved along a line generally parallel to a patient reclining on a table top positioned intermediate the source and the receptor. An engaging structure is provided in the ceiling of each of the plurality of rooms in the building structure to receive and prevent the lateral movement of the distal end of the neck when the neck is moved to the second operative position.

In another embodiment of my invention, I provide a portable X-ray machine including a base, a plurality of ground-engaging wheels attached to the base; a neck having a distal end and mounted in the base for adjustment between at least two operative positions, a first operative storage position, and a second operative extended position with the distal end moved a selected distance away from the base; a source of X-rays; an image receptor for receiving X-rays; an arm having a first end attached to the X-ray source and a second end attached to the receptor, the arm being shaped such that the source and receptor are spaced apart; and, an articulate linkage assembly interconnecting the base and the arm. The linkage assembly is operable to move simultaneously the arm linearly toward or away from the base, and through an arc generally parallel to the ground such that the arm can be moved along a line generally parallel to a patient reclining on a table top positioned intermediate the source and the receptor.

Turning now to the drawings, which depict the presently preferred embodiment of the invention for the purpose of illustrating the practice thereof but not by way of limitation of the scope of the invention, and in which like reference characters refer to corresponding elements throughout the several views, FIG. 1 illustrates an X-ray imaging system constructed in accordance with the principles of the invention and including an engaging structure 37 fixedly secured to the ceiling 35 of a building structure. Structure 37 includes cylindrical opening 38 sized to slidably receive the distal end 36 and prevent end 36 from moving in any lateral direction, including but not limited to the lateral directions indicated by arrows L and M. The X-ray imaging machine of FIG. 1 includes a base comprised of circular plate 11 and upstanding hollow sleeve 10 fixedly secured to plate 11. Aperture 18 is formed through the outer cylindrical wall of sleeve 10 and slidably receives the cylindrical end 19 of a quick release pin. A plurality of ground engaging wheels 12 to 14 are attached to plate 11. Cylindrical neck or telescoping member 15 is slidably received by sleeve 10 and is provided with a plurality of cylindrical openings 16 which receive the end 19 of the quick release pin. In order to extend neck 15 in the direction of arrow K, the quick release pin is removed from sleeve 10, neck 15 is slid upwardly the desired distance until an opening 16 aligns with aperture 18, and the end 19 is again inserted through aperture 18 and the aligned opening 16 to secure neck 15 in the desired position. As would be appreciated by those of skill in the art, neck 15 and sleeve 10 can be constructed in any manner which permits neck 15 to be extended and retracted with respect to sleeve 10. For example, sleeve 10 can be internally threaded and neck 15 externally threaded so that neck 15 can be turned out of and back into sleeve 10.

If desired, sleeve 10 can include a cylindrical member 39 received and stored inside sleeve 10. Member 39 can be downwardly extended from sleeve 10 until the lower end of member 39 contacts and frictionally engages the ground or floor and acts to prevent plate 11 from moving laterally. Any desired prior art construction of member 39 and sleeve 10 can be utilized to enable member 39 to be extended and retracted from sleeve 10 and to be temporarily secured in fixed position pressing against the floor.

C-shaped arm 28 includes a first upper end connected to an X-ray image receptor unit 29 and includes a second end connected to an X-ray source or generation unit 30. The construction and operation of units 29 and 30 is well known in the art and will not be delineated herein. An articulated linkage assembly interconnects C-shaped arm 28 and the base of the apparatus. The articulated linkage assembly includes collar 20, hinge 31, elongate arm 21, hinge 32, elongate arm 22, hinge 33–34, arm 23, hinge 25–26, and arcuate hollow sleeve 27. Collar 20 is mounted on sleeve 10, typically by using a ball bearing assembly to interconnect sleeve 10 and collar 20, and can be manually rotated around the vertical longitudinal axis of sleeve 10 and neck 15 in the directions indicated by arrows F. Set screw 41 enables collar 20 to be secured in a desired position on sleeve 10. Hinge 31 interconnects collar 20 and arm 21. Hinge 32 interconnects arms 21 and 22. Hinge 33–34 interconnects arms 22 and 23. Hinge 25–26 interconnects arm 23 and sleeve 27. Hinge 31 permits pivoting in the directions indicated by arrows A; hinge 32 permits pivoting in the directions indicated by arrows B; hinge 33–34 permits pivoting in the directions indicated by arrows C; and, hinge 25–26 permits pivoting in the directions indicated by arrows D. Arm 28 is slidably received by sleeve 27. Set screw 42 is used to secure arm 28 in a selected position in sleeve 27. As would be appreciated by those of skill in the art, hinges 32 and 33–34 can each be replaced by a "universal" hinge assembly which permits pivoting of arms 22 and 23 in a vertical plane(s), as well as in the horizontal planes indicated by arrows B and C.

Arm 21 can be pivoted in the direction of arrow M and arm 22 pivoted in the direction of arrow N to move arm 28, receptor unit 29, and generator unit 30 linearly in the direction of arrow L toward the base of the X-ray imaging machine. As would be appreciated by those of skill in the art, other pivoting movements of arms 21 and 22 can be used to move arm 28 along a line toward or away from the base of the X-ray imaging machine.

Arms 23 and 28 can be pivoted through an arc J parallel to the ground by simultaneously pivoting arm 23 and 28 about hinge 33–34 in one of the directions indicated by arrow C in FIG. 1. In FIG. 1, arms 21 and 22 are parallel to the ground, though they need not be and can sloped with respect to the ground or floor. When hinges 32 and 33–34 are universal hinges, arms 22 and 23 can be pivoted in vertical planes to positions having varying degrees of slope or cant with respect to the horizontal. When arm 28 is in the vertical orientation depicted in FIG. 1, arm 28 can be pivoted through an arc J parallel to the ground by, while not pivoting arm 21 about hinge 31 or arms 21–22 about hinge 32 or arms 22–23 about hinge 33–34, manually turning collar 20 about sleeve 10 in one of the directions indicated by arrows F. Arm 28 and arm 23 can also be pivoted through an arc J by, when arm 28 is in the vertical orientation depicted in FIG. 1, turning arm 23 about hinge 33–34 in the directions indicated by arrows J.

A particular advantage of the articulated linkage system of the invention is that it permits arm 28 to be moved along a line generally parallel to the ground, to the longitudinal axis X of an examination table spaced apart from the X-ray machine such that axis X is in a tangential relationship to the outer cylindrical surface of sleeve 10, and to a patient reclining on an examination table top 40. Consequently, as shown in FIGS. 2 and 3, arm 28 can be moved linearly in the directions indicated by arrows G and H. Arm 28 can be moved in the directions indicated by arrows G and H because arm 28 can be simultaneously moved along an arc and moved linearly toward and away from the base of the X-ray imaging machine.

In use, while the X-ray imaging machine of FIG. 1 is being transported, arms 21 and 22 are folded such that arm 28 is positioned next to sleeve 10 and the center of gravity of the machine is positioned over and above plate 11. This minimizes the risk that the machine will tip over during transport. Neck 15 and neck 39 are retracted during transport. When the X-ray imaging machine arrives at a room provided with an engaging structure 37 in the ceiling, the X-ray machine is positioned beneath the structure 37 and neck 15 is extended until distal end 36 slides into opening 38. The quick release pin is then used to secure and anchor neck 15 in position with end 36 in opening 38. Anchoring end 36 in opening 38 prevents the X-ray machine from being laterally displaced. If desired, member 39 is extended downwardly toward the floor to frictionally engage the floor and is fixed in position. An engaging structure similar to structure 37 can be formed in or on the floor to slidably receive the lower end of member 39 and prevent member 39 from moving laterally. After distal end 36 is secured in opening 38, arm 28 is be moved outwardly from adjacent sleeve 10 to a position similar to that shown in FIGS. 1 and 2. In FIG. 2, the receptor unit 29 is positioned directly above table top 40 and the X-ray generation unit 30 is positioned directly beneath table top 40. A patient (not shown) reclines on table top 40 intermediate top 40 and receptor unit 29. The arm 28 is manually grasped and is moved linearly over table top 40 in the direction of arrows G or H to a desired position or positions. At each desired position or positions the generation unit 30 is activated and the receptor unit 39 receives and analyzes X-rays which pass through the patient and travel to the receptor unit 39. Units 30 and 39 can be continuously operated to produce multiple X-ray images when arm 28 is displaced to move unit 30 in a continuous sweeping motion over a patient from the patient's head to his or her toes. Unit 30 can also be activated when units 30 and 39 are stationary. After the desired number of X-ray images have been generated for the patient, the articulated linkage assembly is pivoted and folded to move arm 28 back to a position adjacent sleeve 10. The neck 15 and member 39 are retracted away from the ceiling and floor, respectively, to their storage positions in sleeve 10. The X-ray imaging machine is then rolled to another room having an engaging structure 37 in the ceiling and the entire process is repeated.

Many structures other than the specific engaging structure 37 illustrated in FIG. 1 can be utilized to receive and immobilize the distal end 36 of neck 15 to prevent the lateral movement of end 36. End 36 can take on any desired shape and dimension to facilitate its engagement with an engaging structure 37. Engaging structure 37 can be mounted on a support arm or other structure which is secured to extends laterally outwardly from a wall. The engaging structure is mounted on the support arm such that the X-ray imaging machine can be positioned beneath structure 37 and the distal end 36 can be upwardly extended into engagement with structure 37 to prevent lateral movement of the X-ray imaging machine. Or, an engaging structure can be formed on or in a wall to engage member 43 (FIG. 1) and to prevent the lateral movement of the X-ray imaging machine in at least one lateral direction and preferably in all lateral directions. Member 43 is fixedly secured to neck 15. If desired, neck 15 and/or member 43 can, as long as the X-ray machine can be freely moved through doorways and hallway in a building, be permanently secured in a fixed position such that when the X-ray machine is placed in a selected position in a room, the engaging structure can be operated to detachably and fixedly engage neck 15 and/or arm 43 to prevent the lateral movement of neck 15 and/or arm 43 and the portable X-ray machine of FIG. 1. For example, engaging structure 37 can be permanently attached to the ceiling with an extendable—retractable linkage assembly which permits structure 37 to be moved vertically downwardly from the ceiling and over the distal end 36 of neck 15 to engage and prevent the lateral movement of end 36.

When neck 15 is raised in the direction of arrow K toward ceiling 35, the flat circular surface 44 at distal end 36 can be forced against a horizontally oriented flat plate or ceiling surface such that frictional forces between surface 44 and the flat plate tend to prevent the lateral movement of neck 15. Such a frictional engagement between end 36 and an engagement structure formed in or comprising ceiling 35 is, while possible, not preferred. Frictional engagements are too readily separated. End 36 is preferably prevented from moving laterally by a physical structure 37 which abuts against a side surface 45 of end 36 and which locks onto and holds end 36 in place by a mechanical means and not simply by friction. Such a mechanical lock can, for example, comprise a quick release pin which passes through a horizontal aperture 46 formed in structure 37 and into an aperture 47 formed in end 36 and opening at side surface 35. In order for end 36 to break free from such a mechanical lock, structure 37 or quick release pin would have to be sheared or otherwise broken.

Having described my invention in such terms as to enable those skilled in the art to understand and practice it and having described the presently preferred embodiment and best mode thereof, I claim:

1. An X-ray system including
   (a) a plurality of examining rooms in a building structure, each of said rooms including a ceiling;
   (b) a portable X-ray machine including
      (i) a base,
      (ii) a plurality of ground-engaging wheels attached to said base,
      (iii) a neck having a distal end and mounted in said base for adjustment between at least two operative positions,
         a first operative storage position, and
         a second operative extended position with said distal end moved a selected distance away from said base,
      (iv) a source of X-rays,
      (v) receptor means for receiving X-rays from said source,
      (vi) an arm having a first end attached to said source and a second end attached to said receptor means, said arm being shaped and dimensioned such that said source and said receptor means are spaced apart,
      (vii) an articulated linkage assembly interconnecting said base and said arm, said linkage assembly being operable to move simultaneously said arm linearly toward or away from said base, and through an arc generally parallel to the ground,
         such that said arm, said source and said receptor means can be moved along a line spaced away from and tangential to said base and generally parallel to a patient reclining on a table top positioned intermediate said source and said receptor means; and,
   (c) engaging means in said ceiling of each of said plurality of rooms for receiving and preventing the lateral movement of said distal end of said neck and said base when said neck is moved to said second operative position and said arm is moved along said line.

2. A portable X-ray machine including
   (a) a base including a vertically extendible neck having a distal end adapted to be releasably anchored in the ceiling in a room to prevent lateral movement of said neck and said base;
   (b) a plurality of ground-engaging wheels attached to said base;
   (c) a source of X-rays;
   (d) receptor means for receiving X-rays from said source;
   (e) an arm having a first end attached to said source and a second end attached to said receptor means, said arm being shaped and dimensioned such that said source and said receptor means are stacked and spaced apart such that a table top and patient reclining on the table top can be positioned intermediate said source and said receptor means and;
   (f) an articulated linkage assembly interconnecting said base and said arm, said linkage assembly being operable to move, while said base is stationary, simultaneously said arm
      (i) linearly toward or away from said base, and
      (ii) through an arc generally parallel to the ground, such that said arm, said source and said receptor means can be moved along a line spaced apart from and tangential to said base and generally parallel to a patient on a table top positioned intermediate said source and said receptor means.

3. An X-ray system including
   (a) a plurality of examining rooms in a building structure;
   (b) a portable X-ray machine including
      (i) a base,
      (ii) a plurality of ground-engaging wheels attached to said base,
      (iii) a source of X-rays,
      (iv) receptor means for receiving X-rays,
      (v) an arm having a first end attached to said source and a second end attached to said receptor means, said arm being shaped and dimensioned such that said source and said receptor means are spaced apart,
      (vi) a linkage assembly interconnecting said base and said arm, said linkage assembly being operable to move simultaneously said arm, said source, and said receptor means along a line spaced apart from and tangential to said base; and, (c) engaging means in each of said plurality of rooms for, when said X-ray machine is in a selected position in each of said rooms, removably fixedly engaging at least a portion of said base and preventing the lateral movement of said base when said arm is moved along said line.

4. The X-ray system of claim 3 wherein said engaging means in each of said rooms is mounted in the ceiling.

5. The X-ray system of claim 3 wherein said engaging means in each of said rooms is mounted in a wall.

* * * * *